United States Patent [19]

Wilkens

[11] 4,392,239

[45] Jul. 5, 1983

[54] X-RAY DIAGNOSTIC SYSTEM FOR ANGIOGRAPHIC X-RAY PHOTOGRAPHIC SERIES

[75] Inventor: Achim Wilkens, Langensendelbach-Braeuningshof, Fed. Rep. of Germany

[73] Assignee: Siemens Aktiengesellschaft, Berlin & Munich, Fed. Rep. of Germany

[21] Appl. No.: 391,709

[22] Filed: Jun. 24, 1982

Related U.S. Application Data

[63] Continuation of Ser. No. 150,601, May 16, 1980, abandoned.

[30] Foreign Application Priority Data

Jun. 22, 1979 [DE] Fed. Rep. of Germany ....... 2925274

[51] Int. Cl.³ .............................................. G01K 1/04
[52] U.S. Cl. .................................... 378/146; 378/151; 378/152; 378/159; 378/172
[58] Field of Search ............... 378/150, 152, 175, 146, 378/172, 151, 174, 159

[56] References Cited

U.S. PATENT DOCUMENTS

| | | | |
|---|---|---|---|
| 2,331,586 | 10/1943 | Waisco | 378/153 |
| 2,999,159 | 9/1961 | Curry | 378/172 |
| 3,069,549 | 12/1962 | Thompson | 378/160 |
| 3,091,691 | 5/1963 | Snow | 378/172 |
| 3,588,511 | 6/1971 | Montagne | 378/175 |
| 3,660,664 | 5/1972 | Pasmeg | 378/159 |
| 3,725,703 | 4/1973 | Bucky | 378/174 |
| 3,934,151 | 1/1976 | Stowe et al. | 378/175 |
| 4,104,529 | 8/1978 | Gaudel | 378/172 |

Primary Examiner—A. E. Smith
Assistant Examiner—Carolyn E. Fields
Attorney, Agent, or Firm—Hill, Van Santen, Steadman, Chiara & Simpson

[57] ABSTRACT

The exemplary disclosure includes a patient support, an x-ray tube with a diaphragm installation comprising diaphragm plates for the limitation of the x-ray beam irradiating the patient, and a cassette changer for x-ray film cassettes. The cassette changer is a large cassette changer for the entire area to be detected. The diaphragm installation exhibits a fixed diaphragm which limits the maximum size of the x-ray beam, and mechanism for the individual, independent adjustment of movable diaphragm plates determining the dimension of the x-ray beam in the longitudinal direction of the patient support.

5 Claims, 3 Drawing Figures

X-RAY DIAGNOSTIC SYSTEM FOR ANGIOGRAPHIC X-RAY PHOTOGRAPHIC SERIES

This is a continuation of application Ser. No. 150,601, filed May 16, 1980, now abandoned.

BACKGROUND OF THE INVENTION

The invention relates to an x-ray diagnostic system for preparation of angiographic x-ray photographic series corresponding to the course of a contrast medium in a vessel system, comprising a patient support, an x-ray tube with a diaphragm installation with diaphragm plates for the delineation of the x-ray beam irradiating the patient, and a cassette changer for x-ray film cassettes.

An x-ray diagnostic system of this type is described e.g. in the German OS No. 19 30 282. In this x-ray diagnostic system, with the cassette changer, only x-ray photographs with a comparatively small format are to be prepared. For tracing the contrast medium, for example from the abdominal area into the legs, it is therefore necessary to shift the patient support with the patient in a longitudinal direction. On principle, it would be possible to dispense with the longitudinal movement of the patient support if a cassette changer with cassettes is employed whose size covers the entire area of interest; for example, from the abdomen to the feet. However, in this case it is important to insure that the patient is not exposed to unnecessary radiation.

SUMMARY OF THE INVENTION

The object underlying the invention resides in producing an x-ray diagnostic system of the type initially cited in which, proceeding from the idea of utilizing large cassettes which detect the entire area of interest at one time, the patient is exposed only to necessary image-producing radiation.

In accordance with the invention this object is achieved by virtue of the fact that the cassette changer is a large cassette changer for large cassettes for the entire area to be detected, and that the diaphragm installation exhibits a fixed diaphragm which limits the maximum size of the x-ray beam, and that said diaphragm installation likewise possess means for the individual, independent adjustment of diaphragm plates determining the dimensions of the x-ray beam in the longitudinal direction of the patient support. In the inventive diagnostic system it is possible to precisely match the x-ray beam in the longitudinal direction of the patient support with regard to its impingement only at the respective desired photographic exposure field, and, corresponding to this exposure field, to also select the film in a large cassette such that the patient is penetrated only by necessary image-producing radiation. For the tracing of a contrast medium no table longitudinal movement, but only a cassette change, is required if, in every cassette, the film is positioned corresponding to the desired photographic field and if it is correspondingly selected in its size.

Details of the invention shall be apparent from the subclaims.

The invention shall be explained in greater detail in the following on the basis of an exemplary embodiment illustrated on the accompanying sheets of drawings; and other objects, features and advantages will be apparent from this detailed disclosure and from the appended claims.

DETAILED DESCRIPTION

Figure 1:
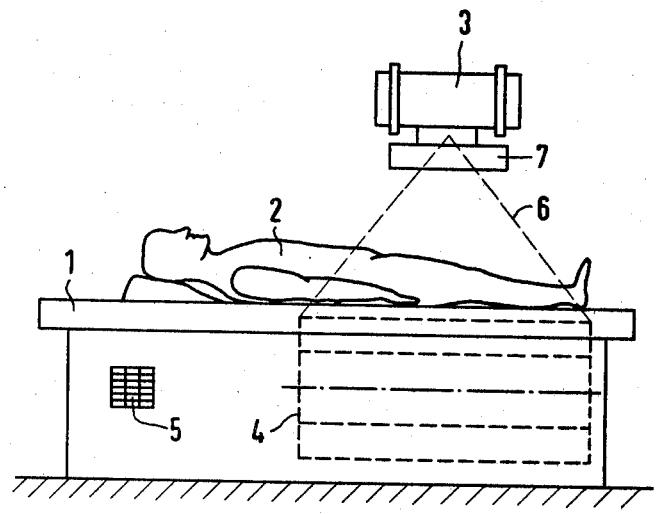
FIG. 1 shows an illustration of an x-ray diagnostic system according to the invention.

In FIG. 1 a patient support 1 is shown on which a patient 2 rests. Angiographic photographs of the patient 2 are prepared in the abdomen-foot area by means of an x-ray tube 3 in conjunction with a cassette changer 4. The cassette changer 4 consists of a cylinder rotatable about a central axis parallel to the longitudinal axis of support 1. The changer 4 has a hexagonal cross-section such that on each of its six exterior surfaces, one large cassette each can be arranged. Thus, for tracing the contrast medium in the patient 2, a maximum of six cassettes can be used.

Figure 2:
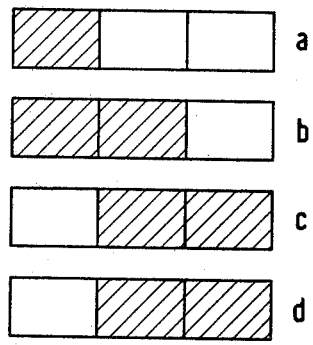
FIG. 2 shows an exemplary illustration of the loading of the cassettes in the case of the x-ray diagnostic system according to FIG. 1 and may be regarded as a diagrammatic development view of the cassette changer peripheral surface to show successive films thereon.

FIG. 2 illustrates by way of example the loading of four cassettes in the cassette changer 4 with films. Each cassette, in its longitudinal direction, can be loaded with one film each in three areas. On surface a of the cassette changer in FIG. 2, the first area viewed from the left is loaded with film; on surface b, the first two areas; and on surfaces c and d the last two areas of the surface are loaded with film. The basis of FIG. 2 is that it suffices for this example to prepare a total of four photographs progressively from the abdomen to the foot of the patient 2. The last two exterior surfaces of the cassette changer 4 are thus not equipped with large cassettes in this example.

In the example according to FIG. 2 the photographic exposure sequence proceeds such that first the keys, corresponding to the cassette changer surfaces a through d of FIG. 2 are depressed in a key field 5, and the x-ray diagnostic system is thus programmed. Subsequently four large cassettes are loaded with films, corresponding to the hatched fields of the surfaces a through d in FIG. 2, and are secured (or mounted) on the cassette changer 4 in the sequence of surfaces a, b, c, d. Now the first photograph according to surface a is made, whereby the x-ray beam 6 is automatically correspondingly restricted. Subsequently the cassette changer 4 is rotated by one step and a photograph according to surface b is made, whereby the restriction of the x-ray beam 6 is again automatically correspondingly varied to cover only the first two film areas of surface b. Subsequently there takes place, pursuant to automatic restriction of the x-ray beam to the active part of the cassette photograph according to surface c, and finally, according to surface d in FIG. 2. During the entire photographic exposure sequence the patient support 1 with the patient 2 is not moved. Due to the automatic shifting of the x-ray beam, always only the area of the patient 2 is irradiated which is also actually of importance for the image production. An unnecessary exposure of the patient to radiation thus does not take place.

Figure 3:
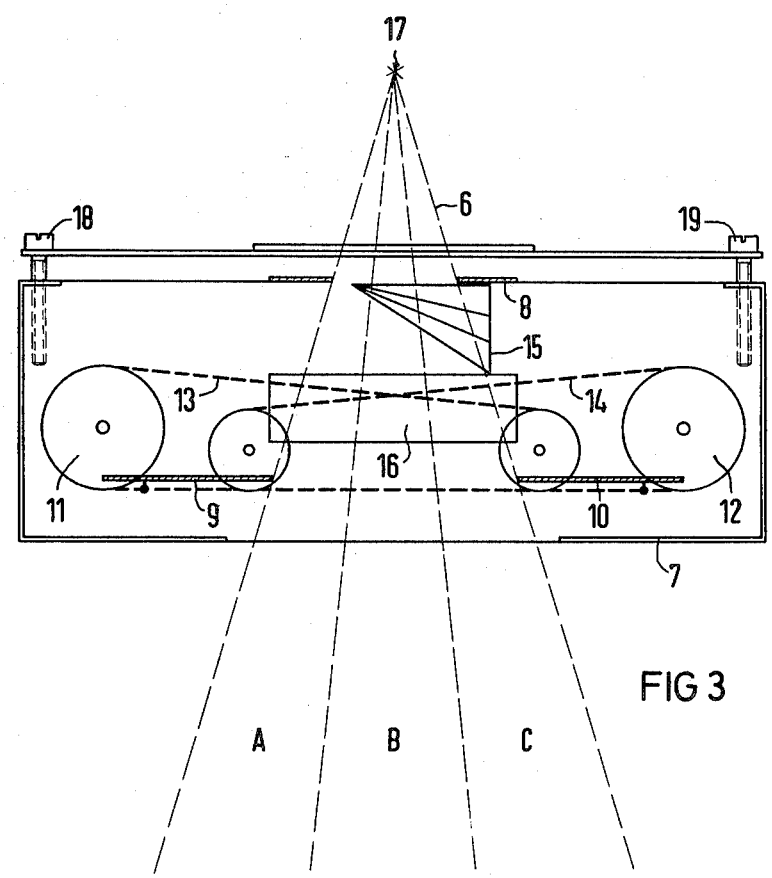
FIG. 3 shows a detail, which is significant in terms of the invention, of the x-ray diagnostic system according to FIG. 1.

In FIG. 3 the diaphragm installation 7 for restricting the longitudinal extent of the x-ray beam 6 is more precisely illustrated. From FIG. 3 it is apparent that the diaphragm installation 7 exhibits a fixed diaphragm 8 which limits the maximum size of the x-ray beam 6. Furthermore, two diaphragm plates 9 and 10 are present which are adjustable in the longitudinal direction of the patient support 1, which are individually adjustable; i.e. independently of one another, by one motor 11 or 12 each, respectively, via associated cables 13 or 14 respectively. The control of the motors 11 and 12 proceeds via the keys in the key field 5; i.e. during selection of the respective radiation fields, the beam of rays 6 is automatically restricted. In FIG. 3, the three partial fields A, B, C, are illustrated. For the example of surface a in FIG. 2, only field A is transmitted by the installation 7; for the example of surface b, the fields A and B are transmitted; for the example of surface c, the fields B and C are transmitted; and for the example of surface d, the fields B and C are likewise transmitted. Accordingly, as illustrated by the above example, the selective movement of the diaphragm plates 9 and 10 causes the longitudinal axes of the respective resultant x-ray beams to change while the x-ray tube 3 remains fixed.

In order to compensate the decreasing subject thickness during the transition from the abdomen to the legs of the patient 2, a wedge filter changer 15 is arranged between the fixed diaphragm 8 and the diaphragm plates 9 and 10. The arrangement of the filter elements of the wedge filter changer 15 relatively close to the focus 17 of the x-ray tube 3 is herein termed a "close-to-focus" arrangement of the wedge filter changer 15. By means of the wedge filter changer 15 different filters with a wedge-shaped progression can be selectively introduced for the x-ray radiation corresponding to the thickness reduction of the subject. Taking into account the decreasing subject thickness during the transition from photographs in the abdominal area to photographs in the leg area can also proceed in that an installation for switching-over the x-ray tube voltage in dependence upon the dimensions of the x-ray beam, which are selected on the key fieldd 5, is provided such as is described in principle in the German OS No. 19 30 282. The subject thickness compensation can also proceed jointly by means of wedge filters and a correspondingly lesser x-ray tube voltage reduction.

Between the fixed diaphragm 8 and the adjustable diaphragm plates 9 and 10 the mirror (or reflector) 16 of a light beam localizer is arranged. The mirror 16 can be radiolucent (or radiation-transmissive) and the light-beam localizer can be designed e.g. according to the U.S. Pat. No. 4,060,733.

The distance of the diaphragm installation 7 from the focus 17 of the x-ray tube 3 is adjustable via screws 18, 19, in the x-ray tube housing. Allowance can thereby be made for diverse film-to-focus-distances.

It will be apparent that many modifications and variations may be effected without departing from the scope of the novel concepts and teachings of the present invention.

SUPPLEMENTARY DISCUSSION

As will be apparent from the foregoing detailed description, the switch field 5 may comprise three individual selectors for each position of the cassette changer 4. Thus the top row of three selectors of field 5 may correspond to a first surface a, FIG. 2, of the cassette changer, while the next three succeeding rows may correspond to surfaces b, c and d in FIG. 2. Where radiation field zone A, FIG. 3, is to be active for the first surface a, as shown in FIG. 2, then only the first selector switch is actuated in the first row of field 5, while the first two selector switches are actuated in the second row, and the last two selector switches are actuated for third and fourth rows. With the films loaded in the cassette changer as indicated in FIG. 2, the sequence of operation can be initiated.

A disclosure of an x-ray sequencing system is found in U.S. Pat. No. 4,137,571. With such a system, desired individual steps may be recorded in a programmable storage, and then automatically sequenced under the control of a clock pulse generator and sequence counter. With such a system, the film cassette changer 4 and the diaphragm installation 7 may be placed in an automatic sequence of operating steps such that, with a preparatory step, cassette changer 4 has surface a, FIG. 2 in the active position, and the first row of switch 5 is activated so that motors 11 and 12 are indexed under control of this row to restrict the x-ray beam to zone A, FIG. 3, corresponding to the first section of surface a, FIG. 2, of the cassette changer 4.

With the release of the contrast agent, x-ray source 3, when pulsed, will expose only such first section of surface a, FIG. 2. Thereafter, the changer 4 is indexed to present surface b, FIG. 2, to x-ray source 3, and correspondingly, the second row of switch field 5 becomes active to operate diaphragm plate 10 such that zones A and B, FIG. 3, are both transmitted by plates 9 and 10 to expose films in the first two sections of surface b, FIG. 2, with the next pulsing of the x-ray tube 3.

Thereafter, as the cassette changer 4 is further indexed to present its surface c. FIG. 2, the third row of switches of selector field 5 controls motors 11 and 12, to shift plates 9 and 10, such that zones B and C are transmitted, and so on.

It is apparent that the automatic sequencer need only select the times for indexing of the cassette changer drum 4, the successive positions of changer drum 4 automatically activating the successive corresponding rows of selector field 5, and thus automatically positioning diaphragm plates 9, 10, according to the selected pattern for each position of changer drum 4.

I claim as my invention:

1. An x-ray diagnostic system for the preparation of angiographic x-ray photographic series over an entire area to be detected corresponding to the course of a contrast medium in a vessel system, said x-ray diagnostic system comprising a patient support (1), an x-ray tube (3) having a diaphragm installation (7) including diaphragm plates for the limitation of the x-ray beam irradiating the patient, and a cassette changer for x-ray film cassettes, characterized in that the cassette changer (4) is a cassette changer having film support means of a total longitudinal extent corresponding to the entire area to be detected, and that the diaphragm installation (7) comprises a fixed diaphragm (8) which limits the maximum size of the x-ray beam (6) to a beam configuration covering said entire area to be detected and covering said total longitudinal extent of said cassette changer while the x-ray tube is in a fixed position, individually adjustable diaphragm plates (9, 10) disposed on opposed sides of said x-ray beam for defining therebetween a resultant x-ray beam for irradiating the patient, and means (11, 12) for effecting the individual, independent adjustment of said diaphragm plates (9, 10) for selectively setting the dimension of the resultant x-ray beam in the longitudinal direction of the patient support and for directing the resultant x-ray beam toward selective respective segments of said total longitudinal extent of said cassette changer which segments lie in respective different directions from the x-ray tube requiring corresponding changes in the longitudinal axes of the respective resultant x-ray beams while said x-ray tube remains in said fixed position.

2. An x-ray diagnostic system according to claim 1, characterized in that, in the diaphragm installation (7), a wedge filter changer (15) is arranged close-to-focus for the purpose of compensation of the subject thickness.

3. An x-ray diagnostic system according to claim 1, characterized in that an installation is present for switching-over the x-ray tube voltage in dependence upon the selected dimensions of the x-ray beam (6)

4. An x-ray diagnostic system according to claim 1, characterized in that, between the fixed diaphragm (8) and the adjustable diaphragm plates (9, 10) a mirror (16) of a light-beam localizer is arranged.

5. An x-ray diagnostic system according to claim 1, characterized in that means (18, 19) are present for the adjustment of the distance of the diaphragm installation (7) from the focus (17) of the x-ray tube.

* * * * *